(12) United States Patent
Blackhurst et al.

(10) Patent No.: US 9,993,146 B2
(45) Date of Patent: *Jun. 12, 2018

(54) SCOPE WARMING DEVICE

(71) Applicant: Fisher & Paykel Healthcare Limited, Auckland (NZ)

(72) Inventors: Michael Joseph Blackhurst, Auckland (NZ); Laurence Gulliver, Auckland (NZ); Robert Ashton Murphy, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/746,518

(22) Filed: Jun. 22, 2015

(65) Prior Publication Data

US 2015/0282700 A1 Oct. 8, 2015

Related U.S. Application Data

(63) Continuation of application No. 10/599,584, filed as application No. PCT/NZ2005/000069 on Apr. 5, 2009, now Pat. No. 9,060,676.

(30) Foreign Application Priority Data

Apr. 5, 2004 (NZ) ........................ 532195

(51) Int. Cl.
*A61B 1/00* (2006.01)
*A61B 1/12* (2006.01)
(Continued)

(52) U.S. Cl.
CPC ............ *A61B 1/127* (2013.01); *A61B 1/0008* (2013.01); *A61B 1/00131* (2013.01);
(Continued)

(58) Field of Classification Search
CPC ............ A61B 1/00057; A61B 1/00062; A61B 1/0008; A61B 1/00096; A61B 1/00131;
(Continued)

(56) References Cited

U.S. PATENT DOCUMENTS 4,429,246 A 1/1984 Miyajima
4,722,323 A * 2/1988 Oblon ....................... F25D 5/00
126/263.08

(Continued)

FOREIGN PATENT DOCUMENTS

EP 1 153 567 11/2001
WO WO 1998/57500 12/1998
WO WO 2001/60239 8/2001

OTHER PUBLICATIONS

Apr. 10, 2013 Canadian Office Action for Application No. 2,563,293.

*Primary Examiner* — Ryan Henderson
(74) *Attorney, Agent, or Firm* — Knobbe, Martens Olson & Bear LLP

(57) ABSTRACT

A warming device (30) for warming the lens portion (2) of an optical instrument (I), such as a laparoscope, to a temperature above ambient to prevent lens fogging comprising: a double walled cylindrical tube (3) having an internal wall (3b), and an external wall (3a), an upper surface and an open distal portion (7) with a central cavity (4) therebetween; a protrusion (9) extending from said upper surface, sized and shaped to receive the lens portion; a circular cap (5) sized to attach to said distal portion of said double walled cylindrical tube; and, a heating element (15) enclosed within said central cavity and thermally coupled to said insulation layer.

13 Claims, 5 Drawing Sheets

(51) Int. Cl.
 *G02B 27/00* (2006.01)
 *G02B 23/24* (2006.01)
 *A61B 1/313* (2006.01)

(52) U.S. Cl.
 CPC .............. *A61B 1/121* (2013.01); *A61B 1/313* (2013.01); *G02B 23/2476* (2013.01); *G02B 27/0006* (2013.01); *A61B 1/00057* (2013.01)

(58) Field of Classification Search
 CPC ... A61B 1/00142; A61B 1/00144; A61B 1/05; A61B 1/051; A61B 1/053; A61B 1/06; A61B 1/12; G02B 21/30; G02B 23/2476
 USPC ........ 600/104, 106, 121–125, 156–159, 169; 219/385, 386, 428–437, 528, 529
 See application file for complete search history.

(56) References Cited

U.S. PATENT DOCUMENTS

| | | |
|---|---|---|
| 4,983,798 A | 1/1991 | Eckler et al. |
| 5,111,804 A | 5/1992 | Funakoshi |
| 5,339,800 A | 8/1994 | Wilita et al. |
| 5,351,675 A | 10/1994 | Brodsky |
| 5,365,267 A | 11/1994 | Edwards |
| 5,400,767 A | 3/1995 | Murdoch |
| 5,549,543 A | 8/1996 | Kim |
| 5,651,757 A | 7/1997 | Meckstroth |
| 5,868,666 A | 2/1999 | Okada et al. |
| 5,880,779 A | 3/1999 | Rhynes |
| 5,910,106 A | 6/1999 | Morgan et al. |
| 6,141,037 A | 10/2000 | Upton et al. |
| 6,147,337 A | 11/2000 | Besser |
| 6,229,132 B1 * | 5/2001 | Knetter .................. 219/759 |
| 6,234,635 B1 | 5/2001 | Seitzinger et al. |
| 6,354,992 B1 | 3/2002 | Kato |
| 6,464,633 B1 | 10/2002 | Hosoda et al. |
| 6,789,644 B2 | 9/2004 | Mukaida |
| 7,018,331 B2 | 3/2006 | Chang et al. |
| 7,453,490 B2 | 11/2008 | Gunday |
| 7,537,563 B2 | 5/2009 | Temple |
| 7,764,304 B2 | 7/2010 | Meron et al. |
| 9,060,676 B2 | 6/2015 | Blackhurst et al. |
| 2002/0022762 A1 | 2/2002 | Beane et al. |
| 2003/0052117 A1 | 3/2003 | Iniestra Hernandez |
| 2003/0085072 A1 | 5/2003 | Mukaida |
| 2003/0124277 A1 | 7/2003 | Agarwal et al. |
| 2003/0142753 A1 | 7/2003 | Gunday |
| 2008/0161646 A1 | 7/2008 | Gomez |

* cited by examiner

SCOPE WARMING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation application of U.S. application Ser. No. 10/599,584, filed Oct. 18, 2007, which is a National Phase Application of PCT International Application No. PCT/NZ05/00069, filed Apr. 5, 2005, which claims priority to New Zealand Application No. 532195, filed Apr. 5, 2004, each of which is hereby incorporated by reference in its entirety.

BACKGROUND OF THE INVENTION

Field of the Invention

This invention relates to a lens warming and cleaning device and particularly but not solely to the warming and cleaning of the distal portion of an optical instrument such as a laparoscope prior to insertion into a body cavity to prevent lens fogging.

Description of the Related Art

A number of products are known in the art for warming and cleaning the distal portion of a laparoscope prior to insertion into a body cavity, thereby preventing the lens incorporated at the distal portion of the laparoscope from fogging when the laparoscope is first inserted into a patient thus obstructing the surgeon's view of the patient's internal organs. This fogging is caused as a result of moisture condensing on the laparoscope lens. The lens temperature is below the dew point temperature of the insufflation gas that is pumped into the patient in order to increase the surgeon's work space within the body cavity. The gas temperature is approximately 37° C. as the human body will humidify the gas to approximately 100% relative humidity and raise the gas temperature to body temperature causing micro-droplets of water to condense on the colder laparoscope lens.

WO01/60239 of the University of Massachusetts discloses a lens warming and cleaning device to warm and clean the lens at the distal portion of an optical instrument such as a laparoscope. The lens warming and cleaning device includes a heat conducting tube sized and shaped to receive the lens portion of the laparoscope, a heating element thermally coupled to the exterior of the heat conducting tube and a cleaning member disposed within the conducting tube. The preferred heating element is a heating pad that includes a flexible, air-permeable outer bag that encases a chemical mixture. The chemical mixture when activated generates an exothermic reaction thereby generating sufficient heat to warm the laparoscopic lens to between 45° and 60° C. The cleaning member disclosed is a sponge inserted into the distal end of the heat conducting tube which is moistened with a saline solution plus an additive such as an anti-fogging additive or surfactant. The warming and cleaning device is self-contained and does not require power to operate. The exothermic heating pad can provide sufficient heat for up to six hours or more and needs to be replaced after one operating procedure whilst the remainder of the equipment is sterilized for re-use.

U.S. Pat. No. 6,234,635 issued to Michael R. Seitzlinger and David Platts discloses an apparatus for maintaining a region of the proximal lens of a laparoscope at a temperature greater than ambient to prevent lens fogging during use. The heating device is a pre-sterilized chemical heat pack which when activated, is attached in the region of the proximal lens end of the laparoscope for the duration of the operating procedure thereby ensuring the lens temperature is maintained to above ambient. The heating device is disposable. However with the device attached to the region of the laparoscope proximal lens the extra weight in this region would modify the balance of the equipment in use.

In U.S. Pat. No. 5,549,543 issued to Il G. Kim a defogging apparatus for heating and maintaining the lens and end portion of a laparoscope to above ambient temperature is disclosed. The apparatus includes an internal water filled receptacle for receiving the lens and laparoscope end portion surrounded by a second water filled container mounted onto a heating plate. The heating plate includes a temperature control mechanism which ensures the water in the inner receptacle and outer container is maintained at a constant temperature. Whilst providing an effective and controlled heating device the equipment requires a power source to operate thereby reducing portability and the receptacles must undergo sterilization procedures prior to use.

SUMMARY OF THE INVENTION

It is an object of the present invention to provide a lens warming and cleaning system for warming the lens temperature above ambient which goes some way to overcoming the abovementioned disadvantages in the prior art or will at least provide the industry with a useful choice.

It is a further object of the invention to provide a lens warming device which is disposable and portable within an operating environment.

Accordingly, in a first aspect the present invention consists in a warming device capable of warming the distal portion of an optical instrument including a lens portion comprising:

a double walled cylindrical tube having an internal wall, external wall, upper surface and open distal portion with central cavity there between, a protrusion extending from said upper surface, sized and shaped to receive the lens portion of said optical instrument, a circular cap sized to attach to said distal portion of said double walled cylindrical tube, an insulation layer between said internal wall and said external wall of said double walled cylindrical tube, and a heating element enclosed within said central cavity and thermally coupled to said insulation layer.

In a second aspect the present invention consists in a warming device capable of warming the distal portion of an optical instrument such as a laparoscope comprising:

a double walled cylindrical tube having an internal wall, external wall, upper surface and open distal portion with central cavity there between, a protrusion extending from said upper surface, sized and shaped to receive the lens portion of said optical instrument, a circular cap sized to attach to said distal portion of said double walled cylindrical tube, an insulation layer between said internal wall and said external wall of said double walled cylindrical tube, and a material coating said central circular protrusion.

In a third aspect the present invention consists in a warming device capable of warming the distal portion of an optical instrument such as a laparoscope comprising:

a double walled cylindrical tube having an internal wall, external wall, upper surface and open distal portion with central cavity there between, a protrusion extending from said upper surface sized and shaped to receive the lens portion of said optical instrument, a circular cap sized to attach to said distal portion of said double walled cylindrical tube, an insulation layer between said internal wall and said external wall of said double walled cylindrical tube, a material coating said protrusion, and an input and an output gas tubing connector attached to said double walled cylindrical tube such that in use at least heated insufflation gas is passed through said device thereby warming said central cavity.

In a fourth aspect the present invention consists in an apparatus for calibrating an optical instrument whilst warming the distal portion of an optical instrument such as a laparoscope comprising:

a double walled cylindrical tube having an internal wall, external wall, upper surface and open distal portion with central cavity there between, a protrusion extending from said upper surface sized and shaped to receive the lens portion of said optical instrument, a circular cap sized to attach to said distal portion of said double walled cylindrical tube, an insulation layer between said internal wall and said external wall of said double walled cylindrical tube, a whitening block inserted into the distal portion of said protrusion, and a heating element enclosed within said central cavity and thermally coupled to said insulation layer.

This invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION

The present invention provides a warming device capable of warming the lens portion of an optical instrument, such as a laparoscope, to a temperature above ambient to prevent lens fogging and a means of cleaning the lens during a surgical procedure to remove any biological matter that may adhere to the lens. The lens warming device is self-contained and does not require the attachment of any power source thereby making the device portable for use anywhere within the surgical operating environment.

In particular a lens warming device is described which provides a means for warming the lens portion of an optical instrument to a temperature above ambient temperature for a prolonged period. At any stage during the operating procedure where the surgeon has to withdraw the laparoscope from the body cavity the lens portion is reinserted into the lens warmer to maintain the lens portion temperature above ambient and where a cleaning member is disposed at the distal end of the lens warming device, the lens will be cleaned on contact with the cleaning member. At the end of the operating procedure the lens warming device may be disposed of thereby potentially eliminating the requirement for the equipment to undergo autoclave or other sterilization procedures.

It will be appreciated that the lens warming device as described in the preferred embodiment of the present invention can be used for many forms of surgical optical instruments generally but will now be described below with reference to the surgical optical instrument being a laparoscope.

Figure 1:
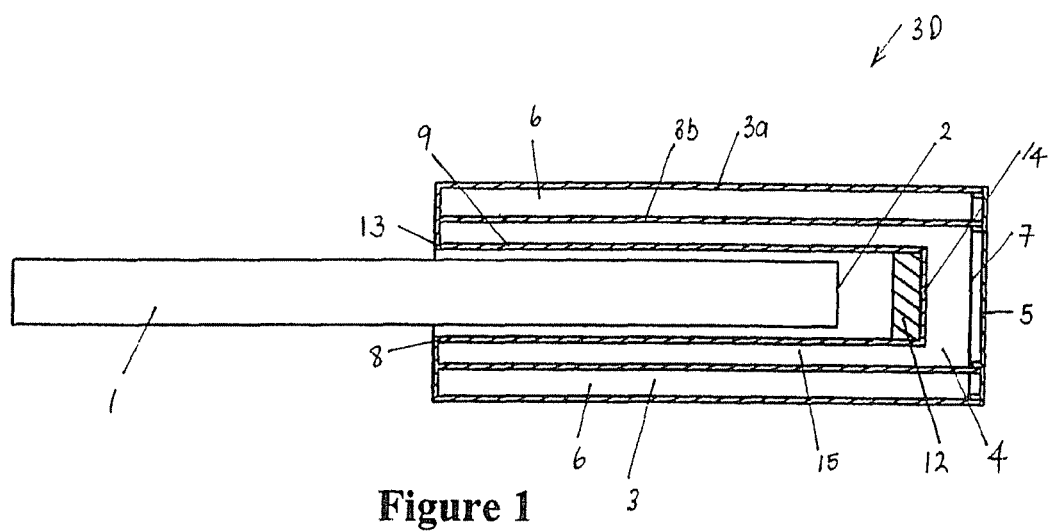
FIG. 1 is a cross-section of the insulated medical lens warming device of the present invention.
Figure 3:
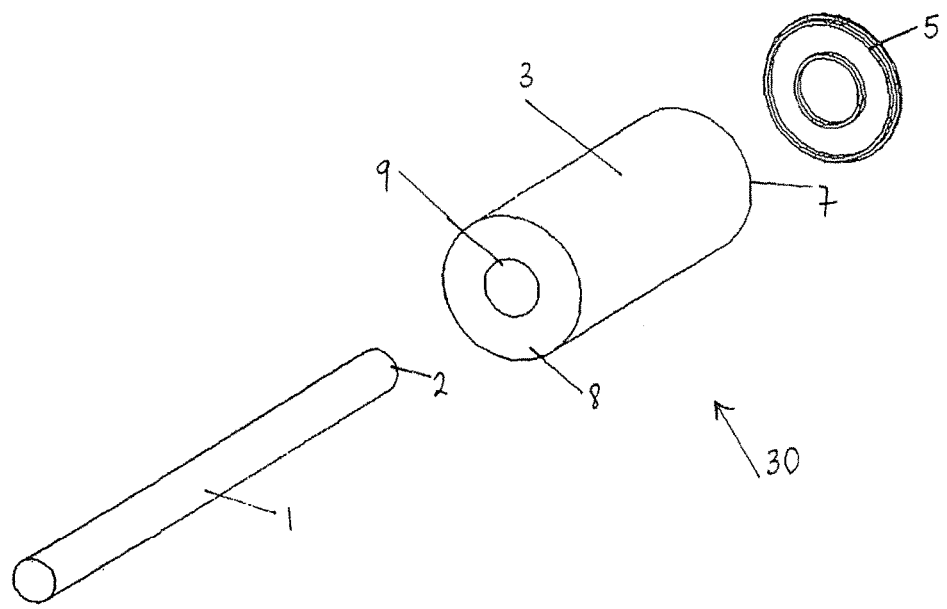
FIG. 3 is an exploded view of the insulated lens warming device of FIG. 1.

With reference to FIGS. 1 and 3, a laparoscope distal portion 1 having a lens 2 at the distal end is shown inserted into the insulated lens warming device 30 of the present invention. The insulated lens warming device 30 is preferably constructed of a thermoplastic or thermoset plastics material such as ABS, polyethylene or other appropriate material. The insulated lens warming device 30 is a double walled cylindrical tube 3a and 3b with central cavity 4, having an open distal portion 7 to which a circular cap 5 is attached by ultrasonic welding, friction fit, snap fit or other appropriate fastening known in the art. Between the inner 3b and outer walls 3a of the double walled cylindrical tube 3 is an insulation layer 6 comprising air. The proximal end 8 of the double walled cylindrical tube 3 is closed and has a protrusion 9 extending into the central cavity 4 towards the distal end 7 of the double walled cylindrical tube 3, sized and shaped to receive the lens portion 2 of the optical instrument 1. The protrusion 9 is preferably a cylindrical protrusion located about the central portion of the proximal end 8 of the double walled cylindrical tube 3. The central cavity 4 is filled with a conductive heating element 15 such as water, saline solution, wheat, oat or barley grass grains, rice, or other appropriate heat conducting material, prior to permanently fitting the circular cap 5 to the distal end 7 of the double walled cylindrical tube 3.

A non-woven cleaning member 12 made from acrylic, polypropylene or other appropriate filter type material may be disposed at the distal end 14 of the cylindrical protrusion 9 such that when the lens portion 2 of the laparoscope 1 is inserted into the cylindrical protrusion 9, the lens portion 2 contacts the cleaning member 12. A similar cleaning member may be provided in anyone of the embodiments of the lens warming device as described herein.

Figure 9:
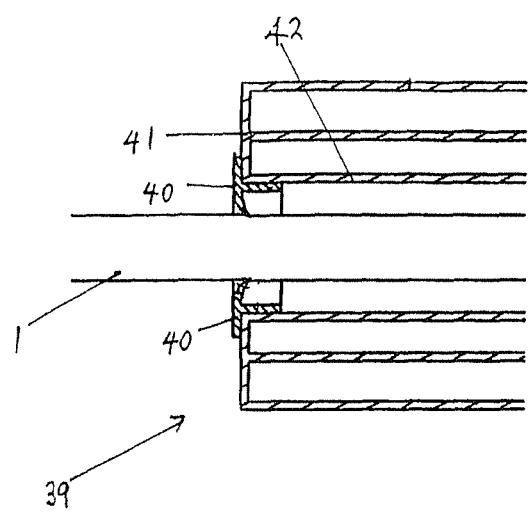
FIG. 9 is a cross-section showing the use of a flexible grommet attached to the insulated lens warming device upper surface of another embodiment of the present invention.

As shown in FIG. 9, the lens warming device 39 may have a flexible grommet 40 made from a plastics based material such as silicon attached at the proximal end 41 of the cylindrical protrusion 42. The flexible grommet 40 enables optical instruments 1 of differing sizes to be inserted into the cylindrical protrusion 42 whilst providing a degree of support for the optical instrument 1. Alternatively or in combination with the flexible grommet 40, the cross-section of the cylindrical protrusion 42 may comprise a plurality of decrementing steps extending from the proximal 41 to the distal portion. This will provide increased support for the optical instrument 1 when it is inserted into the insulated lens warming device 39. The lens warming device 39 is of a similar double cylindrical construction as described above with reference to FIG. 1.

Figure 2:
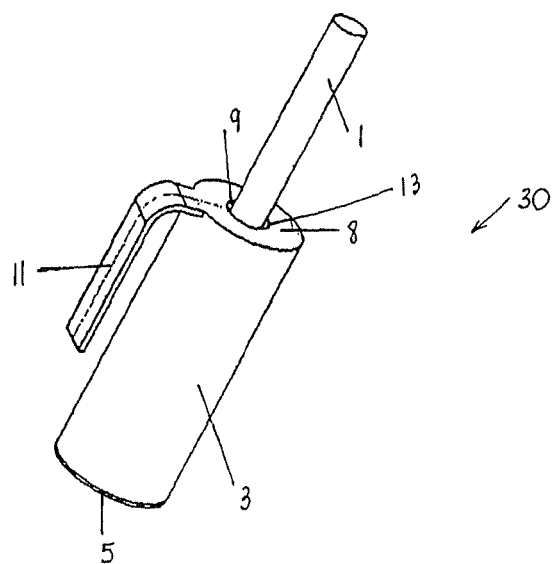
FIG. 2 is a perspective view of the handle clip attached to the insulated lens warming device of FIG. 1.

With reference to FIG. 2 the insulated lens warming device 30 may have a handle 11 of preferably L-shaped configuration, attached to the upper surface 8 of the insulated lens warming device 30. The handle 11 is preferably an integral part of the insulated lens warming device 30 formed during the plastics moulding process however other attachment techniques may be employed such as ultrasonic welding, gluing or other appropriate attachment mechanism. The handle 11 provides a means for transporting the insulated lens warming device 30 around the operating environment as well as providing a means for removably attaching the insulated lens warming device 30 to surgical drapes or table. Alternatively, the handle 11 may comprise a handle clip type mechanism which opens and closes such that the insulated lens warming device 30 can securely grip onto the surgical drapes or table.

Note should be made that any of the embodiments described herein may be provided with a handle as described above in relation to FIG. 2.

Prior to use, the insulated lens warming device 30 is placed in a microwave or other conventional oven type surgical warming device in order to raise the temperature of the heating element 15 to a temperature above ambient body temperature. The cleaning member 12 may then be inserted toward the distal portion 14 of the cylindrical protrusion 9. The lens portion 2 of the laparoscope 2 is then inserted into the cylindrical protrusion 9 such that the lens portion 2 may contact the cleaning member 12. The thermal energy produced by the heating element 15 warms the lens portion 2 to a temperature above ambient such that the lens portion 2 becomes warm enough to prevent lens condensation on insertion of the lens portion 2 into a body cavity while the cleaning member 12 may clean the lens portion 2 in preparation for surgical use.

The insulation layer 6 is in thermal contact with the heating element 15 such that the heating element temperature is maintained for at least the duration of the surgical procedure. Therefore, when the lens portion 2 is removed from the body cavity, it can be reinserted into the insulated lens warming device 30 to maintain the temperature of the lens portion 2 to at least above ambient. Also, when the cleaning member 12 is inserted into the cylindrical protrusion 9 the lens potion 2 may also be cleaned in preparation for reinsertion into the body cavity.

Figure 4:
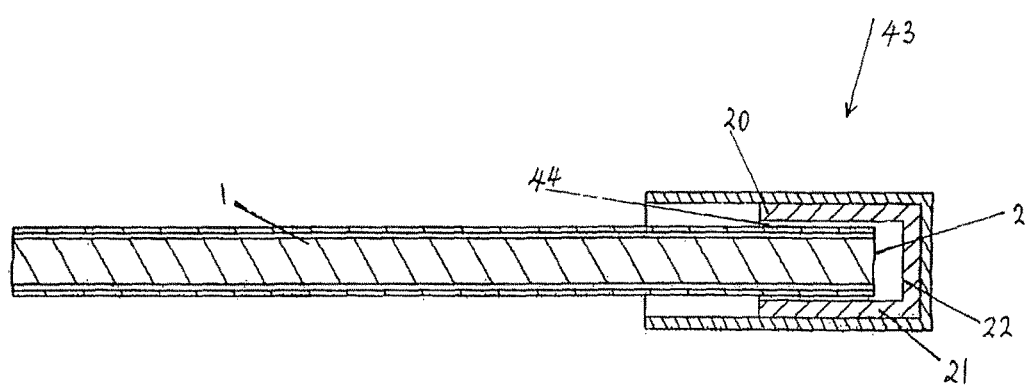
FIG. 4 is a cross-section of a second form of the insulated lens warming device of the present invention.

A second embodiment of the insulated lens warming device 43 of the present invention is shown in FIG. 4. Here the lens portion 2 of an optical instrument 1 is inserted into the insulated lens warming device cylindrical protrusion 44. The walls 20 of the cylindrical protrusion 44 may be impregnated during the plastics moulding and forming process with a black coloured material such as dye. The insulated lens warming device 43 is not pre-heated prior to use as the light source emanating from the lens portion 2 of the optical instrument 1 strikes the distal portion 14 of the cylindrical protrusion 44 and being coated black, absorbs the light energy and converts it to thermal energy due to conduction. The thermal energy therefore warms the lens portion 2 of the optical instrument 1 up to above the dew point of the insufflation gas used within the body cavity thus preventing lens fogging.

Alternatively, instead of impregnating the cylindrical protrusion walls with black dye during the plastics moulding and forming process, a removable black plastic moulded insert 21 of preferably cylindrical cross-section, having a closed distal end 22 may be inserted into the cylindrical protrusion 44. The black insert 21 provides an alternative means of converting light energy into thermal energy due to conduction using the light source emanating from the lens portion 2 of the optical instrument 1.

Figure 5:
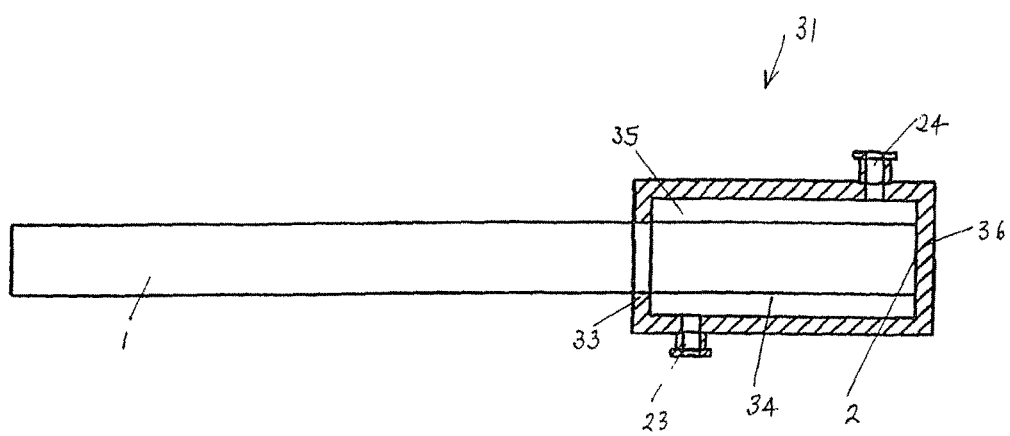
FIG. 5 is a cross-section of a third form of the insulated lens warming device of the present invention.
Figure 6:
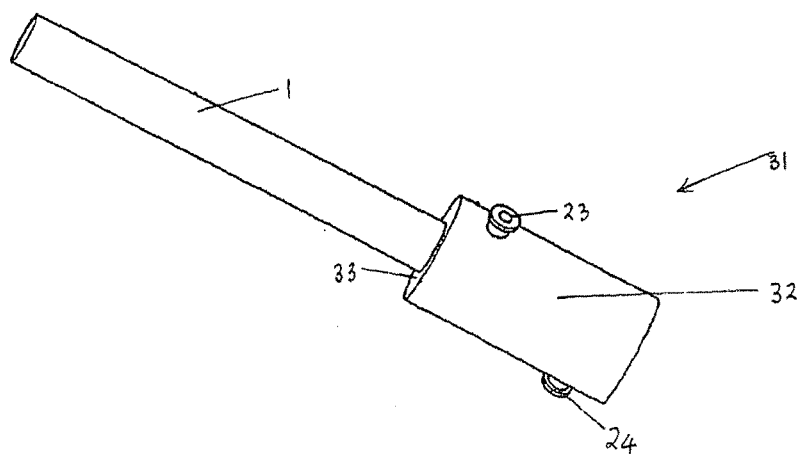
FIG. 6 is a perspective view of the insulated lens warming device of FIG. 5.

An insulated lens warming device of the third embodiment of the present invention is shown in FIGS. 5 and 6. The lens warming device 31 here has two gas tubing connectors 23, 24 in fluid connection with the double walled cylindrical tube 32. The input gas tubing connector 23 is located towards the proximal portion 33 and the output gas tubing connector 24 is located towards the distal portion disposed at substantially 180° to each other, penetrate the body of the double walled cylindrical tube 32. Prior to inserting the lens portion 2 of an optical instrument 1 into the body cavity, a gas tube supplying heated and preferably humidified gas from the same source used to insufflate the body cavity, is diverted and attached to the input gas tubing connector 23 thus inserting at least heated gas into the central cavity 34. The resultant thermal energy generated within the central cavity 34 raises the temperature up to above the dew point temperature of the gas. The thermal energy generated will increase the temperature within the cylindrical protrusion 35 such that when the lens portion 2 of the optical instrument 1 is inserted into the cylindrical protrusion 35 the lens portion 2 absorbs the thermal energy heating the instrument prior to insertion into the body cavity thus preventing lens fogging.

The gas can exit from the central cavity 34 via the output gas tubing connector 24 located towards the distal portion 36 of the insulated lens warming device 31. There is no requirement to attach a gas tube to the second gas tubing connector 24 as the gas is allowed to exit to free air space.

Figure 7:
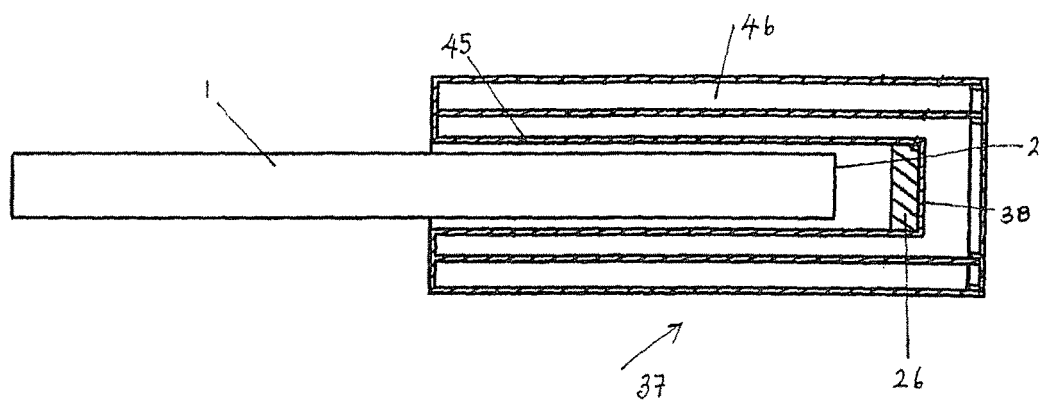
FIG. 7 is a cross-section of a fourth form of the insulated lens warming device of the present invention.

In a fourth embodiment, shown in FIG. 7, the lens warming device 37 preferably has a whitening insert 26 disposed at the distal end 38 of the cylindrical protrusion 45. The whitening insert 26 may be inserted into the cylindrical protrusion 45 prior to the insertion of the lens portion 2 of the optical instrument 1. At the beginning of surgery the optical instrument 1 is switched on such that light emanates from the distal portion of the optical instrument 1. The lens portion 2 is then inserted into the insulated lens warming device 37. As well as being pre-warmed the light emanating from around the distal portion of the optical instrument 1 strikes the whitening insert 26 and is reflected back into the lens portion 2 enabling the equipment to be calibrated to ensure bodily tissue appears the correct colour on insertion of the distal portion of the optical instrument 1 into the body cavity. Note, the general construction of the lens warming device 37 is similar to that of that of FIG. 1 in that the lens warming device 37 has a double walled cylindrical tube construction 46.

The whitening block can be constructed from a thermoset plastics material or a thermoform plastics material. Alternatively, the whitening block can be constructed from a ceramic material. Alternatively, the whitening block can be constructed from a non-woven material or a woven fibrous material.

Figure 8:
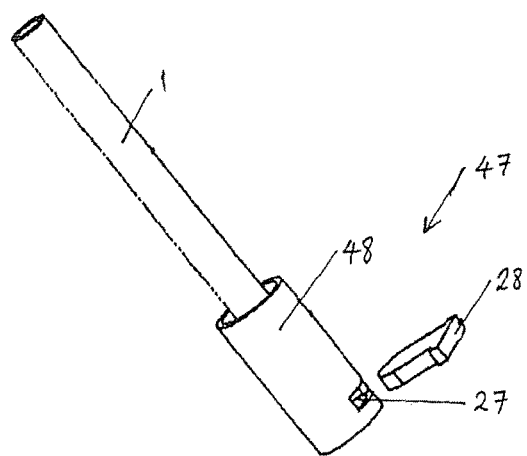
FIG. 8 is a perspective view of the insulated lens warmer of FIG. 7.

Alternatively, as shown in FIG. 8 a cavity 27 may be formed during the plastics moulding process to provide an opening extending from the double walled cylindrical tube outer surface and inner surface, across the distal portion of the cylindrical protrusion (not shown, but similar to 45 in FIG. 7) towards the opposite inner surface wall. Hence, a removable whitening block 28 may be inserted into the double walled cylindrical tube cavity 27 opening such that when the lens portion 2 of a optical instrument 1 is inserted into the insulated lens warming device 47 the scope can be calibrated and warmed prior to insertion into a body cavity. This is achieved by switching on the optical instrument light source such that the lens portion 2 of the optical instrument 1 receives light reflections off the whitening block 1. Again, the general construction of the lens warming device 47 is similar to that of that of FIG. 1 in that the lens warming device 47 has a double walled cylindrical tube construction 48.

What is claimed is:

1. A warming device which warms a distal portion of an optical instrument, the warming device comprising:
    a double walled cylindrical tube having a rigid and uninterrupted internal wall, an external wall, a proximal end, an open distal portion, an insulation chamber between the internal wall and the external wall, and an annular central cavity formed inward in relation to the internal wall;
    a rigid protrusion extending from the proximal end into the annular central cavity, the protrusion sized and shaped to receive a lens portion of the optical instrument;
    a circular cap sized to attach to the distal portion of the double walled cylindrical tube;
    an insulation layer in the insulation chamber between the internal wall and the external wall, the insulation chamber separate from and sealed with respect to the annular central cavity; and
    a heating element enclosed within the annular central cavity.

2. The warming device according to claim 1 wherein the protrusion comprises a plurality of steps of decreasing circumference toward a distal portion of the protrusion.

3. The warming device according to claim 1 wherein the heating element comprises a conductive material.

4. The warming device according to claim 1 wherein the heating element is heated prior to use by microwaving the warming device.

5. The warming device according to claim 1 wherein the heating element is heated prior to use by inserting the warming device into a conventional oven type surgical warmer.

6. The warming device according to claim 1 wherein the insulation layer comprises air.

7. The warming device according to claim 1 wherein the warming device is disposable.

8. The warming device according to claim 1 comprising an attachment mechanism attached to the proximal end of the double walled cylindrical tube, the attachment mechanism configured to removably attach the warming device to a surgical drape or table.

9. The warming device according to claim 1 comprising a flexible grommet surrounding a proximal end of the protrusion.

10. A warming device which warms a distal portion of a surgical optical instrument, the warming device comprising:
    a first cylindrical body having:
        a first end,
        a second closed end, and
        a first radius;
    a second cylindrical body positioned at least partially within the first cylindrical body and having:
        a first end,
        a second end, and
        a second radius smaller than the first radius;
    a third cylindrical body positioned at least partially within the second cylindrical body and having:
        a first opened end,
        a second closed end, and
        a third radius smaller than the second radius, the first opened end of the third cylindrical body comprising an opening configured to receive the distal portion of the surgical optical instrument;
    an annular wall closing the first ends of the first and second cylindrical bodies to form an annularly uninterrupted and sealed insulation chamber between the first and second cylindrical bodies;
    a sealed annularly uninterrupted heating chamber between the second and third cylindrical bodies; and
    a heating element positioned within the sealed annular heating chamber.

11. The warming device according to claim 10 wherein the third cylindrical body comprises a plurality of steps of decreasing circumference toward the closed end of the third cylindrical body.

12. The warming device according to claim 10 comprising a flexible grommet surrounding the first opened end of the third cylindrical body.

13. The warming device according to claim 10 wherein at least one of the first, second, and third cylindrical bodies comprises a thermoplastic or thermoset material.

* * * * *